US009730831B2

(12) United States Patent
Keller

(10) Patent No.: US 9,730,831 B2
(45) Date of Patent: Aug. 15, 2017

(54) METHOD OF MANUFACTURING AN ORAL TRAY FOR STABILIZING JAW JOINT RELATIONSHIPS FOR TREATMENT OF SLEEP APNEA

(71) Applicant: Duane C. Keller, St. Louis, MO (US)

(72) Inventor: Duane C. Keller, St. Louis, MO (US)

(*) Notice: Subject to any disclaimer, the term of this patent is extended or adjusted under 35 U.S.C. 154(b) by 1008 days.

(21) Appl. No.: 13/918,598

(22) Filed: Jun. 14, 2013

(65) Prior Publication Data

US 2013/0334719 A1    Dec. 19, 2013

Related U.S. Application Data

(60) Provisional application No. 61/661,725, filed on Jun. 19, 2012.

(51) Int. Cl.
*A61F 5/00* (2006.01)
*A61F 5/56* (2006.01)
*A61M 16/00* (2006.01)
*A61M 16/04* (2006.01)
*A61M 16/10* (2006.01)

(52) U.S. Cl.
CPC ......... *A61F 5/566* (2013.01); *A61M 16/0057* (2013.01); *A61M 16/0488* (2013.01); *A61M 16/0493* (2014.02); *A61M 16/10* (2013.01)

(58) Field of Classification Search
CPC .................................. A61F 5/566; A61F 5/56
USPC ..................................................... 264/16, 222
See application file for complete search history.

(56) References Cited

U.S. PATENT DOCUMENTS

| 559,251 | A | 4/1896 | Beche, Jr. |
| 4,304,227 | A | 12/1981 | Samelson |
| 5,003,994 | A | 4/1991 | Cook |
| 5,018,533 | A | 5/1991 | Hawkins |
| 5,112,225 | A | 5/1992 | Diesso |
| 5,267,862 | A | 12/1993 | Parker |
| 5,277,202 | A | 1/1994 | Hays |
| 5,313,960 | A | 5/1994 | Tomasi |
| 5,365,945 | A | 11/1994 | Halstrom |
| 5,427,117 | A | 6/1995 | Thornton |
| 5,462,066 | A | 10/1995 | Snyder |
| 5,467,783 | A | 11/1995 | Meade |
| 5,562,106 | A | 10/1996 | Heeke et al. |
| 5,570,704 | A | 11/1996 | Buzzard et al. |
| 5,611,355 | A | 3/1997 | Hilsen |
| 5,642,737 | A | 7/1997 | Parks |
| 5,682,903 | A | 11/1997 | Meade |

(Continued)

OTHER PUBLICATIONS 510-(K) Summary Application and Documents prepared by Cynthia Wright CDT of Sleepwright on Mar. 21, 2011.

(Continued)

*Primary Examiner* — Christina Johnson
*Assistant Examiner* — Xue Liu
(74) *Attorney, Agent, or Firm* — Polster Lieder

(57) ABSTRACT

A method of manufacturing an oral appliance for treating sleep apnea of a patient that has a monolithic body with an upper tray with an upper recess formed to conform to the maxillary teeth of the patient and a lower tray with a lower recess formed to conform to the mandibular teeth, the monolithic body defining a coupling of a rear portion of the upper tray to a rear portion of the lower tray at an angle forming a orifice between front mandibular teeth and front maxillary teeth.

33 Claims, 8 Drawing Sheets

(56) References Cited

U.S. PATENT DOCUMENTS

| | | |
|---|---|---|
| 5,755,219 A | 5/1998 | Thornton |
| 5,816,799 A | 10/1998 | Parker |
| 5,823,193 A | 10/1998 | Singer et al. |
| 5,829,441 A | 11/1998 | Kidd et al. |
| 5,868,138 A | 2/1999 | Halstrom |
| 5,884,628 A | 3/1999 | Hilsen |
| 5,915,385 A | 6/1999 | Hakimi |
| 6,041,784 A | 3/2000 | Halstrom |
| 6,055,986 A | 5/2000 | Meade |
| 6,129,084 A | 10/2000 | Bergersen |
| 6,161,542 A | 12/2000 | Halstrom |
| 6,305,376 B1 | 10/2001 | Thornton |
| 6,325,064 B1 | 12/2001 | Thornton |
| 6,516,805 B1 | 2/2003 | Thornton |
| 6,729,335 B1 | 5/2004 | Halstrom |
| 6,766,802 B1 | 7/2004 | Keropian |
| 6,848,905 B2 | 2/2005 | Jacobs et al. |
| 6,983,752 B2 | 1/2006 | Garabadian |
| 7,146,982 B2 | 12/2006 | Mousselon et al. |
| 7,178,529 B2 | 2/2007 | Kownacki |
| 7,311,103 B2 | 12/2007 | Jeppesen |
| 7,451,767 B2 | 11/2008 | Keropian |
| 7,597,103 B2 | 10/2009 | Thornton et al. |
| 7,721,741 B2 | 5/2010 | Thornton |
| 7,730,891 B2 | 6/2010 | Lamberg |
| 7,748,386 B2 | 7/2010 | Thornton |
| 7,757,693 B2 | 7/2010 | Toussaint |
| 8,123,519 B2 | 2/2012 | Schultz |
| 2002/0139375 A1 | 10/2002 | Kulick |
| 2003/0217753 A1 | 11/2003 | Thornton |
| 2004/0177852 A1 | 9/2004 | Abramson |
| 2004/0177853 A1 | 9/2004 | Kownacki |
| 2005/0199247 A1 | 9/2005 | Garabadian |
| 2006/0040236 A1* | 2/2006 | Schmitt ............. A61C 13/0004 433/213 |
| 2006/0130850 A1 | 6/2006 | Chen |
| 2006/0289013 A1 | 12/2006 | Keropian |
| 2007/0028926 A1 | 2/2007 | Kotani |
| 2007/0235037 A1 | 10/2007 | Thornton |
| 2008/0000483 A1 | 1/2008 | Halstrom |
| 2008/0041396 A1 | 2/2008 | Lucker |
| 2008/0060659 A1 | 3/2008 | Bonato et al. |
| 2008/0072915 A1 | 3/2008 | Nelissen |
| 2008/0190437 A1 | 8/2008 | Hervy-Auboiron |
| 2008/0210244 A1 | 9/2008 | Keropian |
| 2008/0236597 A1 | 10/2008 | Bergersen |
| 2009/0007922 A1 | 1/2009 | Harrington |
| 2009/0056724 A1 | 3/2009 | Keropian |
| 2009/0120448 A1 | 5/2009 | Keropian |
| 2009/0178684 A1 | 7/2009 | Greenburg |
| 2009/0188510 A1 | 7/2009 | Palmer |
| 2009/0223525 A1 | 9/2009 | Thornton |
| 2009/0241969 A1 | 10/2009 | Walker |
| 2009/0272387 A1 | 11/2009 | Spencer |
| 2009/0301500 A1 | 12/2009 | Abramson |
| 2010/0018538 A1 | 1/2010 | Sotos et al. |
| 2010/0065066 A1 | 3/2010 | Hamburg |
| 2010/0065067 A1 | 3/2010 | Lee |
| 2010/0139667 A1 | 6/2010 | Atkinson et al. |
| 2010/0154802 A1 | 6/2010 | Fuselier |
| 2010/0242969 A1 | 9/2010 | Lyons |
| 2010/0263676 A1 | 10/2010 | Thornton |
| 2010/0269835 A1 | 10/2010 | Thornton |
| 2010/0300457 A1 | 12/2010 | Horchover |

OTHER PUBLICATIONS

510(k) Summary Application and Documents prepared by Carolyn Thomas of Speciality Appliances on Sep. 2008 and amended Jan. 2009, pp. 5-1 to 5-4 and 4-1.

* cited by examiner

METHOD OF MANUFACTURING AN ORAL TRAY FOR STABILIZING JAW JOINT RELATIONSHIPS FOR TREATMENT OF SLEEP APNEA

CROSS-REFERENCE TO RELATED APPLICATIONS

This application claims the benefit of U.S. Provisional Application No. 61/661,725, filed on Jun. 19, 2012, the disclosure of which is incorporated herein by reference.

FIELD

The present disclosure relates to devices and methods for of manufacturing thereof, more specifically, to methods of manufacturing an oral tray for treatment of sleep apnea.

BACKGROUND

The statements in this section merely provide background information related to the present disclosure and may not constitute prior art.

Sleep apnea is a sleep disorder characterized by abnormal pauses in breathing or instances of abnormally low breathing, during sleep. Each pause in breathing can last from a few seconds to minutes, and may occur many times in an hour of sleep. Sleep apnea is diagnosed in an overnight sleep test or study. Common symptoms include loud snoring, interrupted breathing, restless sleep, and sleepiness during the daytime. Sleep apnea is recognized as a problem due the sufferer having daytime sleepiness and fatigue, slower reaction time, vision problems and other cognitive and behavioral effects, such as moodiness, belligerence, decreased attentiveness and motivation.

Treatments for sleep apnea include lifestyle changes, such as avoiding alcohol or muscle relaxants, losing weight, quitting smoking, sleeping at a 30-degree elevation of the upper body, sleeping in a lateral position (sleeping on a side as opposed to supine positions such as sleeping on the back), surgical procedures to remove and/or tighten tissue in the airway, and use of an oral appliance that keeps the airway open during sleep, and/or positive airway pressure systems to promote air transfer during sleep. These oral appliances include both passive and positive airway pressure devices/assemblies.

Presently, dental trays are used for multiple applications in dentistry, including dental tooth movements, topical medication delivery, mandibular positioning and intra-oral orthotics and cosmetic purposes, as components of sleep apnea appliances to advance the mandible and multiple other uses. Trays used for periodontal treatment are affixed to the patient's teeth with custom formed seals to provide a comfortable means of attachment to the individual dental arch. Dental trays are often used as mouth guards or other types of appliances to help manage bite relationships, mandibular maxillary relationships or to serve for tooth protection. Orthotics are a type of dental appliances used to acquire the patient's ideal or best functional relationship for an optimal joint, muscle, head/neck and upper quadrant association. A dental tray can be used in conjunction or in place of an orthotic once the best functional relationship is established, but dental trays fabricated from EVA material are extremely difficult to adjust if there is any change to the bite or other change to the patient. The functional dental relationships are confirmed in stone, plaster, computer generated or other means of reproducing the dental conditions and the models or other reproduced means are approximated at the orthotic determined best functional relationship. Trays are fabricated and affixed to one another at this relationship to maintain the best functional joint, muscle and structural and functional positioning for patients when they sleep so they will maintain the optimal functional relationships.

SUMMARY

The inventor hereof has succeeded at designing a dental tray, the method of use and the method of manufacture for the treatment of sleep apnea such as the treatment of restricted or obstructive airway that occurs during sleep that results from a decreased airway due to abnormal mandibular/maxillary relationships and soft tissue alterations.

According to one aspect, a method of manufacturing an oral appliance for treating sleep apnea of a patient is disclosed. The patient has maxillary teeth located on an upper jaw, mandibular teeth on a lower jaw, a mouth cavity formed by the upper jaw and the lower jaw containing the maxillary teeth, the mandibular teeth, a tongue and an airway defined by the throat passage. The method of manufacturing the oral applicant includes taking an upper impression of the maxillary teeth and a soft gum tissue proximate to and surrounding the maxillary teeth of the patient, and preparing a maxillary cast from the upper impression. The method also includes taking a lower impression of the mandibular teeth and a soft gum tissue proximate to and surrounding the mandibular teeth of the patient and preparing a mandibular cast from the lower impression. The method further includes determining a functional position of the lower jaw relative to the upper jaw of the patient to open the airway defined by the throat passage; preparing an upper tray from the maxillary cast and preparing a lower tray from the mandibular cast. The method includes embedding the upper tray in stone forming an upper tray stone cast leaving only a portion of the upper tray exposed, embedding the lower tray in stone forming a lower tray stone cast and leaving only a portion of the lower tray exposed. The method further includes placing the embedded upper tray and the embedded lower tray in an articulator, positioning the embedded upper tray and the embedded lower tray in the articulator for alignment in the determined functional position and coupling the exposed portion of the upper tray to the exposed portion of the lower tray forming an oral appliance having a unified body with the upper tray being positioned relative to the lower tray at the functional position. The method further includes removing the stone in which oral appliance is embedded.

A method of manufacturing an oral appliance for treating sleep apnea of a patient having maxillary teeth located on an upper jaw, mandibular teeth on a lower jaw, a mouth cavity formed by the upper jaw and the lower jaw containing the maxillary teeth, the mandibular teeth, a tongue and an airway defined by the throat passage. The method includes the steps of taking an upper impression of the maxillary teeth and a soft gum tissue proximate to and surrounding the maxillary teeth of the patient, taking an impression of the tongue of the patient, preparing a maxillary cast from the upper impression, taking a lower impression of the mandibular teeth and a soft gum tissue proximate to and surrounding the mandibular teeth of the patient, preparing a mandibular cast from the lower impression. determining a functional position of the lower jaw relative to the upper jaw of the patient to open the airway defined by the throat passage, preparing an upper tray from the maxillary cast, preparing a lower tray from the mandibular cast, preparing a tongue support fixture from the tongue impression, embedding the upper tray in stone forming an upper tray stone cast, said embedding the upper tray leaving only a portion of the upper tray exposed, embedding the lower tray in stone forming a lower tray stone cast, said embedding the lower tray leaving only a portion of the lower tray exposed. placing the embedded upper tray and the embedded lower tray in an articulator, positioning the embedded upper tray and the embedded lower tray in the articulator for alignment in the determined functional position, coupling the exposed portion of the upper tray to the exposed portion of the lower tray forming an oral appliance having a unified body, coupling the tongue support to at least one of the exposed portion of the upper tray and the exposed portion of the lower tray to form a unibody oral appliance with integrated tongue support, and removing the stone in which oral appliance is embedded.

A method of manufacturing an oral appliance for treating sleep apnea of a patient having maxillary teeth located on an upper jaw, mandibular teeth on a lower jaw, a mouth cavity formed by the upper jaw and the lower jaw containing the maxillary teeth, the mandibular teeth, a tongue and an airway defined by the throat passage. The method including the steps of: taking an upper impression of the maxillary teeth and a soft gum tissue proximate to and surrounding the maxillary teeth of the patient and includes taking an impression of a soft gum tissue proximate to and surrounding the maxillary teeth of the patient, preparing a maxillary cast from the upper impression including the soft gum tissue proximate the maxillary teeth, taking a lower impression of the mandibular teeth and a soft gum tissue proximate to and surrounding the mandibular teeth of the patient and includes taking an impression of a soft gum tissue proximate to and surrounding the mandibular teeth of the patient, preparing a mandibular cast from the lower impression including the soft gum tissue proximate the mandibular teeth, determining a functional position of the lower jaw relative to the upper jaw of the patient to open the airway defined by the throat passage, preparing an upper tray from the maxillary cast including a portion covering the soft gum tissue proximate to and surrounding the maxillary teeth, preparing a lower tray from the mandibular cast including a portion covering the soft gum tissue proximate to and surrounding the mandibular teeth, wherein preparing at least one of the upper tray and the lower tray includes forming a seal a portion covering the soft gum tissue proximate to and surrounding the maxillary teeth or mandibular teeth respectively, embedding the upper tray in stone forming an upper tray stone cast, said embedding the upper tray leaving only a portion of the upper tray exposed, embedding the lower tray in stone forming a lower tray stone cast, said embedding the lower tray leaving only a portion of the lower tray exposed, placing the embedded upper tray and the embedded lower tray in an articulator, positioning the embedded upper tray and the embedded lower tray in the articulator for alignment in the determined functional position, coupling the exposed portion of the upper tray to the exposed portion of the lower tray forming an oral appliance having a unified body, and removing the stone in which oral appliance is embedded.

Further aspects of the present disclosure will be in part apparent and in part pointed out below. It should be understood that various aspects of the disclosure may be implemented individually or in combination with one another. It should also be understood that the detailed description and drawings, while indicating certain exemplary embodiments, are intended for purposes of illustration only and should not be construed as limiting the scope of the disclosure.

BRIEF DESCRIPTION OF THE DRAWINGS

It should be understood that throughout the drawings, corresponding reference numerals indicate like or corresponding parts and features.

DETAILED DESCRIPTION

Figure 1A:
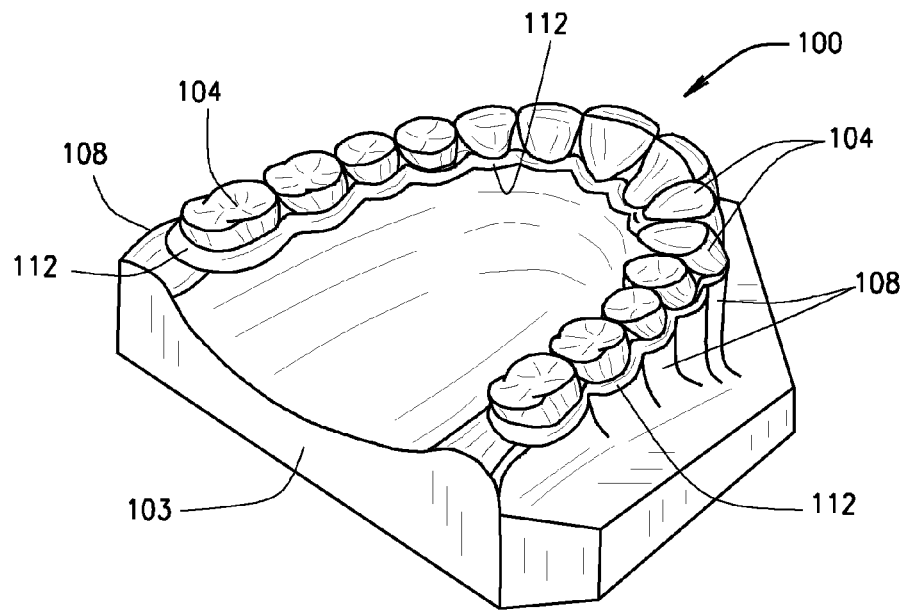
FIG. 1A is a cast formed from an impression of maxillary teeth of a patient for formation of an upper tray and FIG. 1B is a cast formed from an impression of mandibular teeth for formation of a lower tray for forming the unified sleep apnea appliance according to one exemplary embodiment. As shown herein, is the option with the groove for forming the optional seal along the gum line.

The following description is merely exemplary in nature and is not intended to limit the present disclosure or the disclosure's applications or uses.

Before turning to the figures and the various exemplary embodiments illustrated therein, a detailed overview of various embodiments and aspects is provided for purposes of breadth of scope, context, clarity, and completeness.

A oral appliance for treating sleep apnea of a patient including a monolithic body having an upper tray with an upper recess formed to conform to the maxillary teeth of the patient and a lower tray having a lower recess formed to conform to the mandibular teeth, the monolithic body defining a coupling of a rear portion of the upper tray to a rear portion of the lower tray at an angle forming a orifice between front mandibular teeth and front maxillary teeth, the upper tray including a raised upper seal surrounding the recess corresponding to the patient's upper gum line and the lower tray including a raised lower seal surrounding the recess corresponding to the patient's lower gum line each when the patient's teeth are disposed in the recesses.

In another embodiment, an oral appliance for treating sleep apnea of a patient, the patient having maxillary teeth located on an upper jaw with surrounding upper soft gum tissue and an upper gum line, mandibular teeth located on a lower jaw with surrounding lower soft gum tissue and a lower gum line, a mouth cavity formed by the upper jaw and the lower jaw containing the maxillary teeth, the mandibular teeth, a tongue and an airway defined by the throat passage. The appliance has a monolithic body having an upper tray with an upper recess formed to conform to the maxillary teeth of the patient and a lower tray having a lower recess formed to conform to the mandibular teeth. The monolithic body defines a coupling of a rear portion of the upper tray to a rear portion of the lower tray at an angle forming an orifice between front mandibular teeth and front maxillary teeth.

In some embodiments, the upper tray and the lower tray are coupled together to form the monolithic body by an amount of ethylene vinyl acetate (EVA) material positioned between the two trays. The upper tray and lower tray are coupled in a position relative to each other in a determined best functional position of the lower jaw relative to the upper jaw of the patient to open the airway defined by the throat passage as discussed herein.

In some embodiments, the upper tray is coupled to the lower tray in the region from about a first or second premolar back to about a second molar, however, such coupling can vary by patient based on the determined best functional positioning of the jaws.

In some embodiments, the recess of the upper tray conforms to the upper soft gum tissue surrounding the upper teeth and the recess of the lower tray conforms to the upper soft gum tissue surrounding the lower teeth. In such embodiments, the upper tray can include a raised upper seal surrounding the recess corresponding to the patient's upper gum line. The lower tray includes a raised lower seal surrounding the recess corresponding to the patient's lower gum line each when the patient's teeth are disposed in the recesses. In such embodiments, as will be discussed, the appliance as described herein for treatment of sleep apnea can also be used during sleep for application of a bleaching or whitening agent for whitening of the teeth or of a medicament for treatment of periodontal disease.

In some embodiments, the monolithic body includes at least one tongue support customized to conform to the tongue of the patient. By customized, generally this includes a tongue support that has been formed from an impression of the patient's tongue, but can be otherwise customized as necessary to adapt to the particular tongue of the patient. The tongue support can be positioned and dimensioned for holding a back edge of the patient's tongue in a forward position. This can include positioning for inhibiting the backward movement of the tongue when the oral appliance is placed within the mouth of the patient and onto the teeth of the patient. In this manner, not only is the monolithic body holding the upper and lower jaw in a predefined relationship, but the oral appliance further restricts the backward movement of the tongue to further ensure that the throat airway is open during sleep and that the tongue does not obstruct the open airway during use of the appliance.

In some embodiments, there is a single tongue support, that can be positioned between the right and left sides of the appliance, or in other embodiments, there can be two tongue supports, one positioned on each side of the monolithic body and positioned for engaging opposing sides of the tongue when the oral appliance is placed within the mouth of the patient. The tongue support or supports can be coupled to either side between the upper and lower trays or attached to an upper tray or to a lower tray depending on the arrangement as determined to be necessary to position the tongue support for the proper placement relative to the tongue for holding the back edge of the tongue in a forward position. As will be addressed below, the tongue support can be coupled to an inner side portion of at least one of the upper tray and the lower tray with an amount of ethylene vinyl acetate (EVA) material during formation of the monolithic body and/or attachment of the upper tray to the lower tray as will be discussed below. This can include coupling between the rear portion of the upper tray and the rear portion of the lower tray or to one or both of the trays with a desired or necessary amount of ethylene vinyl acetate (EVA) material that is added as a bonding agent. Generally, as the tongue support is in constant contact with the tongue, as with the upper and lower trays, each of these can be formed from a moldable resilient soft plastic elastomeric material or other suitable material. However, in one embodiment, each is formed from the moldable resilient soft plastic elastomeric material so as to be more pleasant and comfortable during use than a harder plastic.

In some embodiments, the appliance can be further adapted by the formation of an adaptive interface at the formed orifice between the front mandibular teeth and the front maxillary teeth, e.g., between the front of the upper tray and the lower tray, so as to enable or provide for the selective coupling to an oral device associated with a sleep apnea positive pressure machine. Such an interface would be customized for attachment to the positive pressure tube, hose, or mask, via an appropriate coupling mechanism for such device as at the current time; there is no defined standardized interface. However, if one is developed, this embodiment could meet such standard and still be within the scope of this disclosure.

In another embodiment, a dental oral appliance assembly for treating sleep apnea of a patient, the patient having maxillary teeth located on an upper jaw with surrounding upper soft gum tissue and an upper gum line, mandibular teeth located on a lower jaw with surrounding lower soft gum tissue and a lower gum line, a mouth cavity formed by the upper jaw and the lower jaw containing the maxillary teeth, the mandibular teeth, a tongue and an airway defined by the throat passage. The appliance has a monolithic body having an upper tray with an upper recess formed to conform to the maxillary teeth of the patient and a lower tray having a lower recess formed to conform to the mandibular teeth. The monolithic body is defined by the coupling of a rear portion of the upper tray to a rear portion of the lower tray at an angle forming an orifice between front mandibular teeth and front maxillary teeth. The monolithic body includes at least one tongue support customized to conform to the tongue of the patient to the hold the tongue when worn by the patient as discussed above in various embodiments thereof. The other embodiments and variations and options as described above would also be applicable to and with the present embodiment.

Figure 1B:
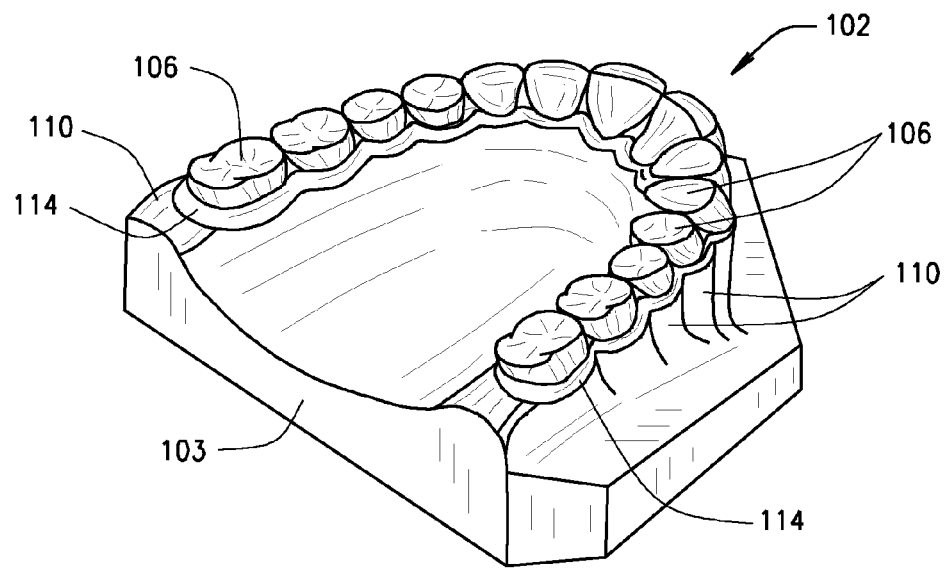

Referring now to the drawings, FIG. 1A is a cast 100 formed from an impression of maxillary teeth of a patient for formation of an upper tray and FIG. 1B is a cast 102 formed from an impression of mandibular teeth for formation of a lower tray for forming the unified sleep apnea appliance according to one exemplary embodiment. As shown, the casts 100, 102 include tooth castings 104 and 106 of the patient's maxillary teeth and mandibular teeth, respectively. The casts 100, 102 Each cast 100, 102 is formed from a base cast 103 to include the tooth castings 104, 106 and surrounding soft gum tissue 108, 110 for the upper cast 100 and the lower cast 102, respectively.

To create the casts 100, 102, a dentist can use any conventional impression-taking technique for example having the patient bite into a container filled with a suitable hardenable material such as an alginate material. When the alginate hardens, an accurate copy of the patient's teeth are formed as the tooth castings 104, 106 along with the adjacent periodontal soft tissue 108, 110 is produced. A suitable hardenable material such as, for example, plaster or dental stone is poured into the impression to create a male casting 100, 102 that includes the tooth castings 104, 106 and the and soft gum tissue 108, 110 which are representative of the patient's teeth and adjacent soft tissue. The casts 100, 102 are made for all or a portion (less than all) of the upper and/or lower teeth. The soft tissues of the oral environment, specifically the tongue, can also be included in the impression and casts 100, 102. Further, the casts 100, 102 can be formed to include connections or adapter for connecting to other fixtures to help control the position of the tongue and posture, or for connecting to other devices such as a continuation positive airway pressure (CPAP) machine.

Further, in embodiments where a gum line seal is desired or required, an upper groove 112 and/or a lower groove 114 is formed in the casts 100, 102, respectively for forming upper and lower seals. The grooves 112, 114 can be formed in the casts 100, 102 after fully cured. The dentist or technician can use a hand-held tool (e.g., a round dental bar of desired dimension in a dental hand piece or laboratory engine) or a dental lathe device, or a computer directed removal device (such as a CAD-CAM) to remove a desired or predefined amount of the stone or plaster material from the casts 100, 102 at locations corresponding to desired level at the patient's gingival or gum line within the soft tissue 108, 110 portion of the casts 100, 102. The depth and magnitude of the removed materials is done in a manner to correspond to the gum line so that only portions of the hardenable material from the casts 100, 102 are removed to create the one or more trough-like recesses or grooves 112, 114 of the desired depth and thickness formed around the front and rear surfaces of the tooth casts 104, 106 within the gum line of the soft gum tissue. In this manner, the grooves 112, 114 assists in subsequent forming of a thickened lingual extension in the trays formed from the casts 100, 102, which is resiliently deflected by the gum when the tray is installed on the patient's upper and lower teeth.

As shown in FIGS. 1A and 1B, by way of example, the casts 100, 102 include most of the upper and lower teeth. However, it should be understood that less the all teeth can be molded and casts 100, 102 and the subsequently formed upper and lower trays can be formed using less than all of the maxillary and mandibular teeth. Further, the grooves 112, 114 do not need to be formed as the tray seal is an optional feature of the upper and lower trays.

Figure 2A:
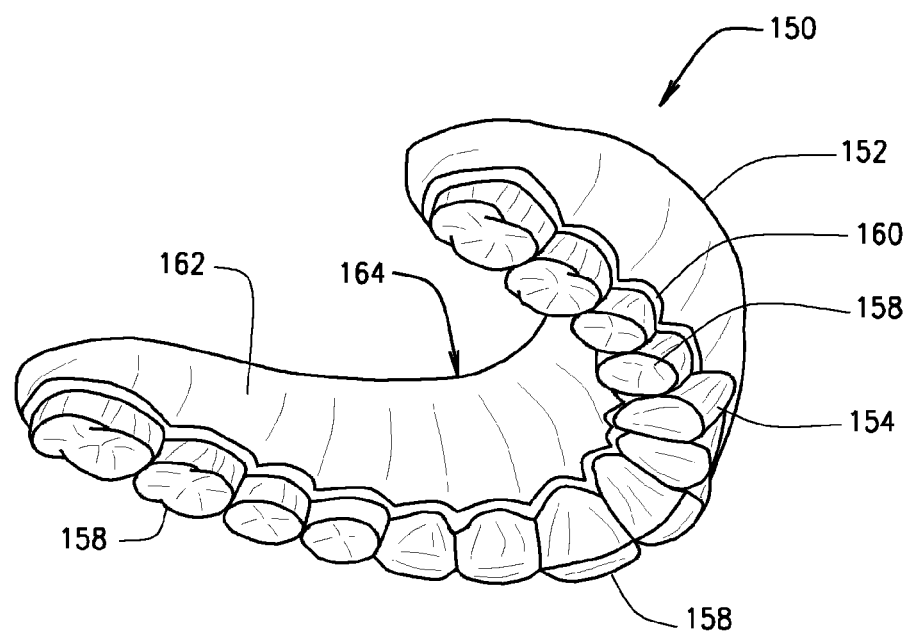
FIG. 2A is an upper tray formed from the cast of FIG. 1A

FIGS. 2A (top view) and 3A (bottom view) are illustrations of one embodiment of an upper tray 150 formed from the cast 100 of FIG. 1A according to one exemplary embodiment for formation of a sleep apnea appliance. As shown here, an upper tray 150 has a molded body 152 the forms a concave cavity 154 that includes an upper recess 156 that forms upper tray crown covers 158 of the maxillary teeth of the patient by formation from the upper tooth casts 104 of the upper cast 100. The molded body 152 includes upper tray body extension 162 which is the portion of the molded body 152 surrounding and supporting the upper recess 156. In those embodiments requiring such, an upper gum line seal 160 is formed between the upper recess 156 and the upper tray body extension 162. Further in some embodiments, as will be described in further detail below, a portion of the molded body 152 and/or the upper tray body extension 162 can be formed as a tongue support 164 or portion thereof, or in the alternative, can be formed to provide a physical/structural support for a tongue support that is subsequently attached or coupled thereto.

Figure 2B:
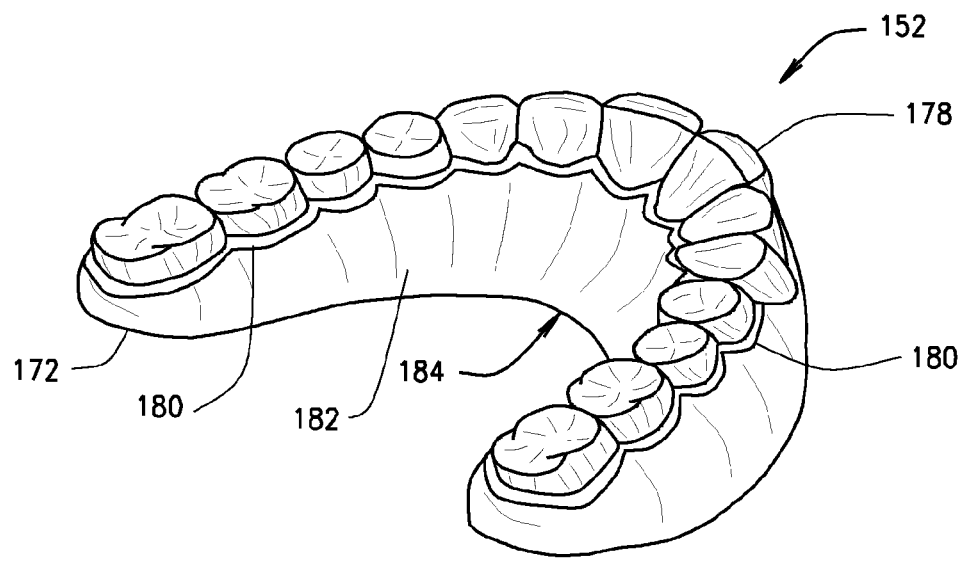
FIG. 2B is a lower tray formed from the cast of FIG. 1B according to one exemplary embodiment of the sleep apnea appliance.
Figure 3A:
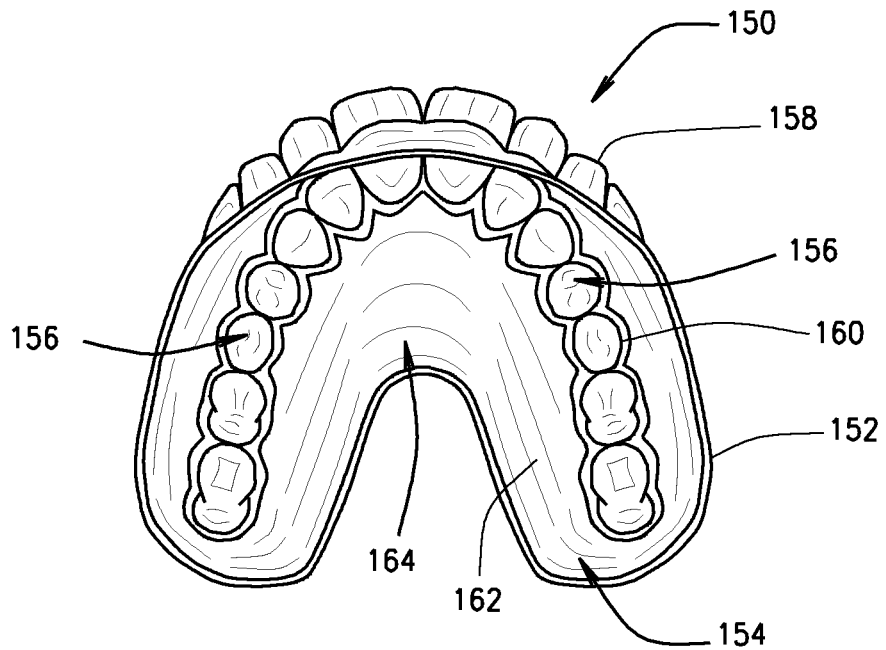
FIG. 3A is a bottom view of the upper tray formed from the cast of FIG. 1A
Figure 3B:
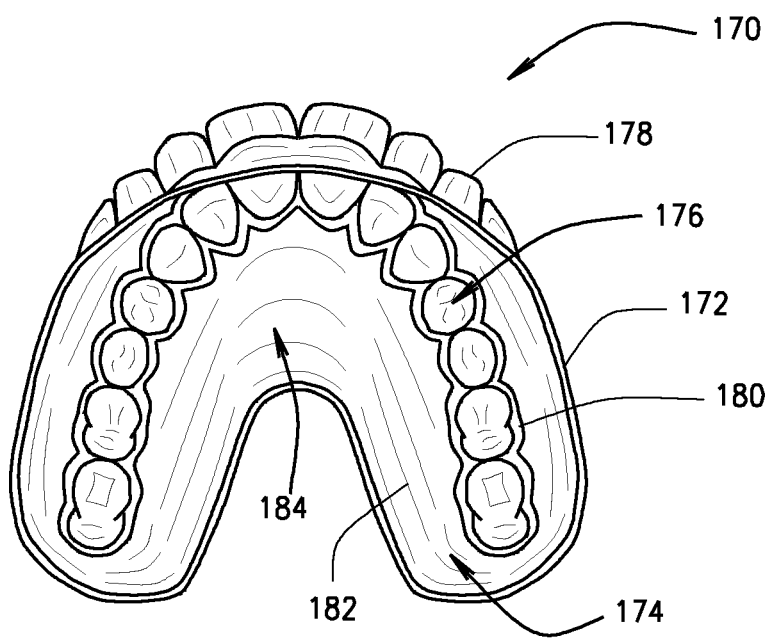
FIG. 3B is a bottom view of the lower tray formed from the cast of FIG. 1B each showing the recess in which the teeth will be placed and showing the optional gum line seals according to one exemplary embodiment of the sleep apnea appliance.

Similarly, FIGS. 2B (top view) and 3B (bottom view) illustrate one embodiment of a lower tray 170 formed from the cast 102 of FIG. 1B according to one exemplary embodiment for formation of a sleep apnea appliance. As shown here, an lower tray 152 has a molded body 172 the forms a concave cavity 174 that includes a lower recess 176 that forms lower tray crown covers 178 of the mandibular teeth of the patient by formation from the lower tooth casts 106 of the lower cast 102. The lower molded body 172 includes lower tray body extension 182 which is the portion of the lower molded body 152 surrounding and supporting the lower recess 176. In those embodiments requiring such, a lower gum line seal 180 is formed between the lower recess 176 and the lower tray body extension 182. Further in some embodiments, as will be described in further detail below, a portion of the lower molded body 172 and/or the upper tray body extension 182 can be formed as a tongue suppressor 184 or portion thereof, or in the alternative, can be formed to provide a physical/structural support for a tongue support that is subsequently attached or coupled thereto.

The seal 160 and 180 are optional. As shown in these figures, a full body 152, 172 is formed to cover the associated gums, and such is not required in all embodiments. Each upper tray 150 and lower tray 170 is configured with recesses 156, 176 in which the teeth of a sleep apnea patient will be placed so that they are covered by the crown covers 158, 178. In these exemplary embodiments, the optional gum line seals 160, 180 are shown, which can aid in securing the appliance formed from trays 150, 170 to the teeth, gums and jaws of the patient during sleep apnea treatment. As shown, a substantial portion of the gums can be covered by the trays 150, 170, but such is not required in all embodiments, and in some embodiments, only the gum line proximate to the teeth are covered by the trays 150, 170 and in other embodiments, the trays only cover the teeth or the crowns of the teeth.

Figure 4:
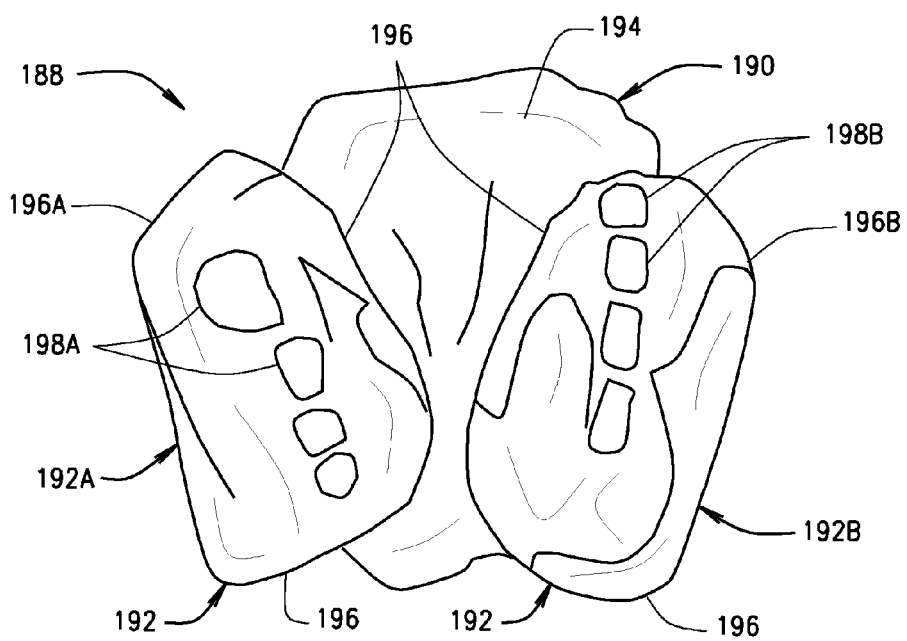
FIG. 4 is a top schematic view of a wax impression of a bite registration and of a patient's tongue placed thereon for formation of a tongue support for one exemplary embodiment of the sleep apnea appliance.

FIG. 4 is a top schematic view of a wax impression 188 of a bite registration 192 and of a tongue registration 190 for formation of a tongue support 164, 184 for one exemplary embodiment of the sleep apnea appliance. As shown, there is a left bite registration 192A formed from a left wax body 196A with left tooth bite impressions 198A from the left teeth of the patient. There is a right bite registration 192B formed from a right wax body 196B with right tooth bite impressions 198B from the right teeth of the patient. The tongue registration 190 is formed with a tongue wax body 194 from an impression or modeling of the patient's tongue during the bite and the registration thereof. While FIG. 4 is only an top view of the wax impression 188 and showing only the right and left tooth impressions 198A, 198B of the maxillary teeth, it should be understood that the left bite registration 192A, the right bite registration 192B, and the tongue registration 194 will include not only the registration of the left and right maxillary teeth and the upper or top of the tongue as shown in this top view, but also the mandibular teeth and the lower or bottom of the tongue that is similarly reflected on the opposing sides of the thereof, but not shown in FIG. 4's top view. In this manner, not only is a registration of the patient's maxillary and mandibular teeth taken during a normal bite, the position of the maxillary teeth in relation to the mandibular teeth, and therefore the jaws containing the teeth, as well as the position of the tongue during a bite.

The wax bite impression 188 with the bite registration 192 and the tongue registration 190 is used to determining an angle alpha $\alpha$ which is the angle between the maxillary/upper teeth and the mandibular/lower teeth during a normal bit. This can be used to determine an appliance angle beta $\beta$ which is the desired angle for the position of the upper tray 150 relative to the lower tray 170 from back to front (towards the opening of the mouth) to form the sleep apnea appliance for the particular patient for appropriate sleep apnea treatment through the use thereof. The wax bit impression 188 is also used to determine an amount of offset $\epsilon$ between the lower jaw and the upper jaw during the normal bite which can be used to determine a desired appliance offset $\sigma$ for the upper tray 150 relative to the lower tray 170 of the sleep apnea appliance. The amount of the appliance angle beta $\beta$ and the amount of the appliance offset $\sigma$ can be determined by the health care specialist during determining the appropriate relative positions of the jaws for sleep apnea treatment and control (minimization of restricted airways in the throat, jaws and mouth) during treatment or use of the sleep apnea appliance. Further, the tongue impression 190 can be used to determine the need for, design of and placement of the tongue support 164, 184 or pair of opposing supports 164, 184 for the sleep apnea appliance.

Figure 5:
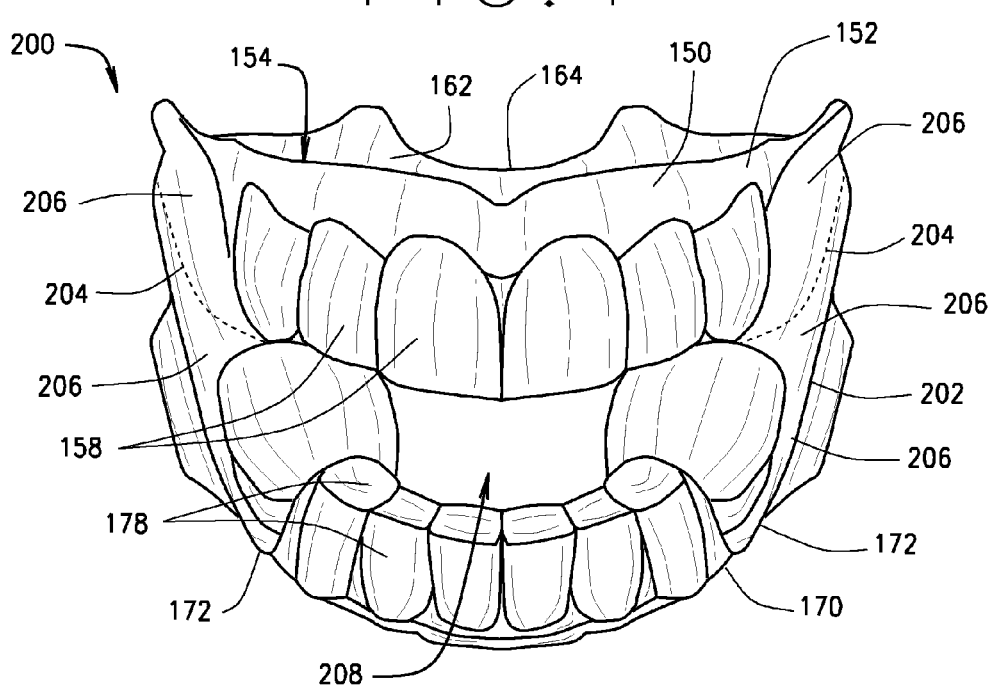
FIG. 5 is a front schematic illustration of a sleep apnea appliance according to one exemplary embodiment showing the tongue support and the angle of opening for the orifice and the coupling of the upper tray to the lower tray at angle beta and coupling using the coupling compound for forming the monolithic appliance.
Figure 6:
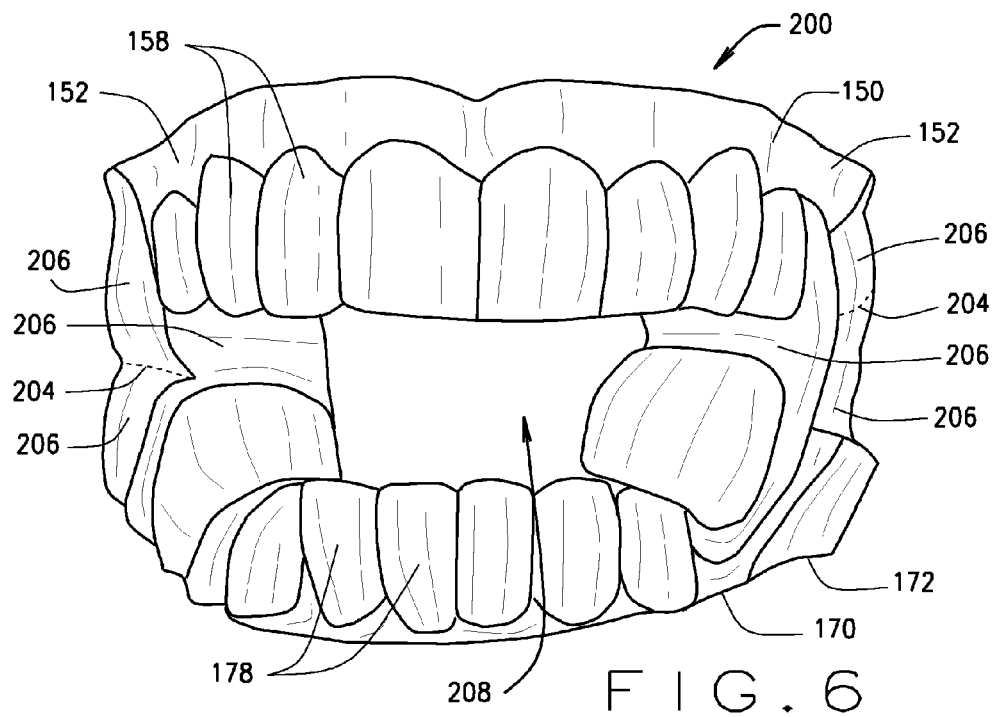
FIG. 6 is a front schematic illustration from a photograph of a sleep apnea appliance according to one exemplary embodiment showing the EVA coupling material and without the tongue support.

FIGS. 5 and 6 are front schematic illustration of a sleep apnea appliance 200 according to one exemplary embodiment. In this illustrated exemplary embodiment, the appliance 200 has a monolithic body 202 that is formed by coupling the upper tray 150 to the lower tray 170 along a coupling interface 204 at the rear portion of the upper tray 150 and the rear portion of the lower tray 170 on both the left and right sides of each. As shown in this example, a coupling compound 206 forms the coupling interface 204 when the coupling compound 206 is applied to the upper portion of the lower tray 170 and the lower portion of the upper tray 150 during manufacture of the appliance 200. As shown in this example, the coupling compound 206 can be an amount of ethylene vinyl acetate (EVA) material that is positioned between the two trays 150, 170 and is then cured to form the monolithic body 202 of the sleep apnea appliance 200. In designing and forming the monolithic body 202, the determined appliance angle beta $\beta$ and the amount of the appliance offset $\sigma$ (not labeled in FIG. 5's front view) defines an airway cavity 208. The assembled appliance 200 having the monolithic body 202 includes both the upper recess 156 in the upper tray 150 for receiving the patient's maxillary teeth and the lower recess 176 in the lower tray 170 for receiving the patient's mandibular teeth when the patient places the appliance 200 on such for sleep apnea treatment. In the exemplary embodiment of FIG. 6, as compared to FIG. 5, a portion of the upper tray 150 includes the tongue support 164 at a rear portion thereof for supporting the patient's tongue during treatment.

Figure 7:
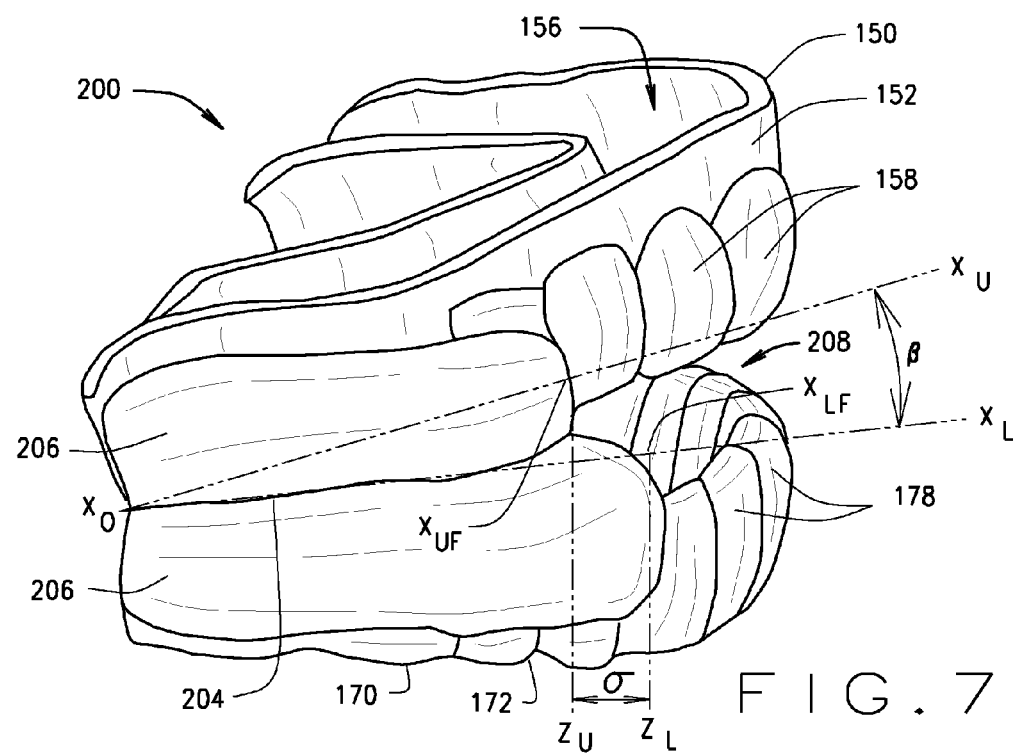
FIG. 7 is a side schematic illustration from a photograph of a sleep apnea appliance according to one exemplary embodiment showing the upper recess for the upper teeth and the tongue support and the opening angle beta for forming the front orifice.
Figure 8:
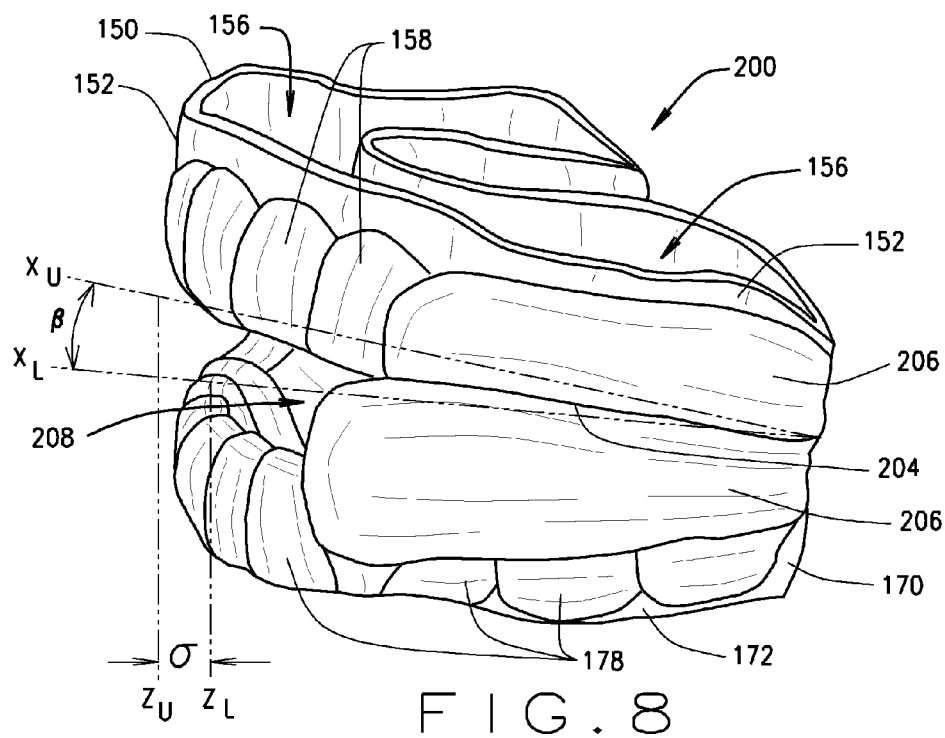
FIG. 8 is a schematic illustration from a photograph of a sleep apnea appliance according to one exemplary embodiment showing the best functional relationship with the lower tray being placed forward of the upper tray by offset distance and the angle of opening beta to form the orifice.

FIGS. 7 and 8 are top side perspective schematic views of sleep apnea appliances 200 according to two exemplary embodiments. Theses illustrated embodiments is similar to that of FIGS. 5 and 6, but as a perspective view, have been labeled to illustrate the monolithic body 202 of the appliance 200 having the upper tray 150 is a predetermined position relative to the lower tray 170. Two sets of relationship axis have been included. The axis XL is along the longitudinal line from the back to the front of the lower tray 170 that can be approximated by a center between the left side and right side thereof or can be two parallel lines one on each lateral side thereof. The axis XU is along the longitudinal line from the back to the front of the upper tray 150 similarly positioned. The upper tray longitudinal axis XU intersects the lower tray longitudinal axis XL at the rear or proximate the rear or back of each of the upper tray 150 and lower tray 170, identified as $X_O$. As described herein, the appropriate appliance angle beta $\beta$ is defined by the medical care provider and the upper tray 150 is coupled to the lower tray 170 to form the monolithic body 202 fixing the angle beta $\beta$ as the angular relationship between the two trays 150, 170. This also defines the appliances' airway cavity 208 as shown. FIG. 7 further includes vertical plane or line $Z_U$ defining a front $X_{UF}$ of the upper tray 150 or the maxillary teeth or jaw of the patient associated therewith. For illustration purposes, the front $X_{UF}$ is the distance point along longitudinal line $X_U$ from the intersection $X_O$. The vertical plane or line $Z_L$ defines a front $X_{LF}$ of the lower tray 150 or the mandibular teeth or jaw of the patient associated therewith. For illustration purposes, the front $X_{LF}$ is the distance point along longitudinal line $X_L$ from the intersection $X_O$. The difference in the distance between the two front positions $X_{UF}$ and $X_{LF}$ is the appliance offset $\sigma$ that is specified by the medical care provider as identified or defined for sleep apnea treatment for the particular patient. FIG. 7 defines these two front positions $X_{UF}$ and $X_{LF}$ and therefore the appliance offset $\sigma$ as related to a lateral portion of both the upper and lower trays 150, 170 as they may associate with a position of the jaw containing the upper and lower canine, by way of example. FIG. 8 provides a different exemplary determination by defining the two front positions $X_{UF}$ and $X_{LF}$ and therefore the appliance offset $\sigma$ as related to a front foremost portion of the mammalian such as the front most positioning of the central incisor. As will be understood to those of skill in the art, these are only two examples of alignments and that others are also possible based on the particular needs as determined during evaluation. Whatever alignment points or placements is used during the preparation of the wax impression 188 of the bit registration 192 and tongue registration 190 (where provided) would be alignment points or placements used herein.

Figure 9:
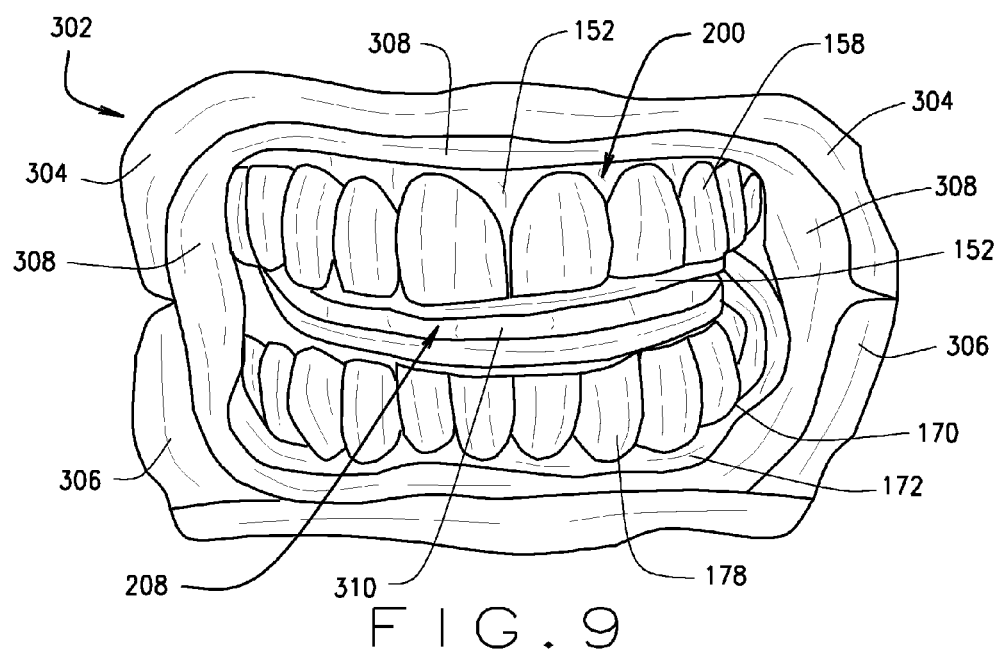
FIG. 9 is a schematic illustration from a photograph of a sleep apnea appliance in use in the mouth of a patient according to one exemplary embodiment.
Figure 10:
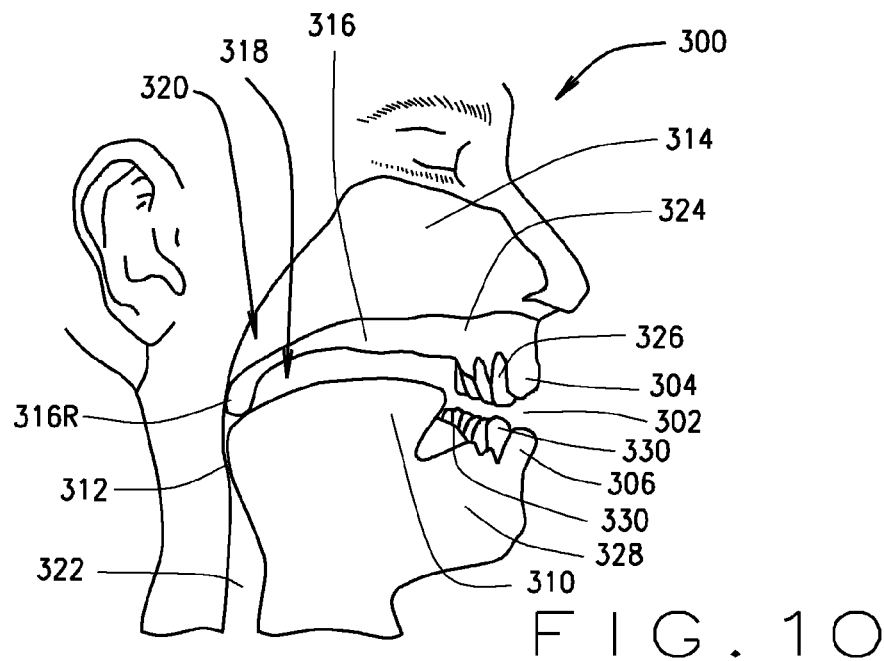
FIG. 10 is a side diagram of a patient suffering from sleep apnea with a closed airway.

FIG. 9 is a schematic illustration from a photograph of a sleep apnea appliance 200 as in actual use in a mouth 302 of a patient 300 according to one exemplary embodiment. The patient's mouth 302 includes upper lips 304 and lower lips 306, as well as mouth soft tissue 308 generally known as buccal mucosa or lip and cheek lining. As shown, the appliance 200 is placed about the patients teeth and the patient's tongue 310 is illustrated within the airway cavity 208 of the appliance for illustration purposes. FIG. 10 is a side view diagram of a patient 300 suffering from sleep apnea with a closed airway 312. As shown and known in anatomy, each patient has a nasal cavity 314, a palate 316 with rear portion 316R, an oral cavity 318, a pharynx 320, a esophagus 322, maxillary/upper jaw 324 with maxillary/upper teeth 326, and mandibular/lower jaw 328 with mandibular/lower teeth 330. As shown, the air passage way or pharynx 320 in FIG. 10 is shown as largely or substantially closes along with a portion of the oral cavity at the rear of the tongue 310 proximate to the pharynx 320. In this illustration, the patient 300 has restricted airways that can result in sleep apnea.

Figure 11:
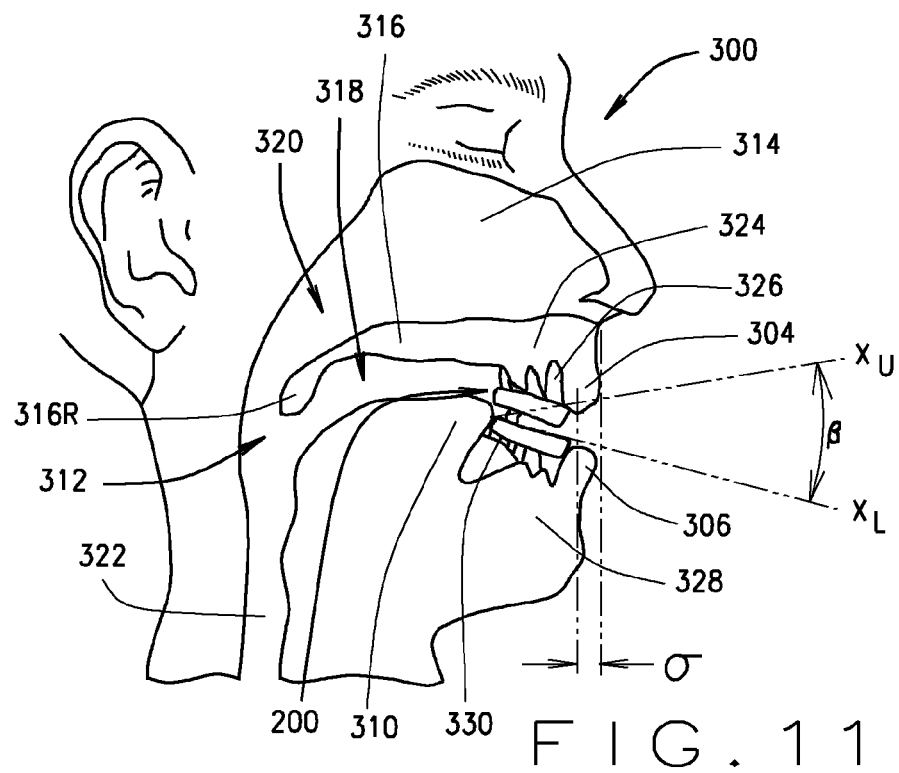
FIG. 11 is a side diagram of the patient of FIG. 10 with the appliance with tongue support in place showing the opening of the mouth at angle beta to form orifice, with the lower jaw and mandibular teeth moved forward of the maxillary teeth and the tongue support holding the tongue forward, thereby opening the airway of the patient as compared to that of FIG. 10.

FIG. 11 is a side view diagram of the patient of FIG. 10 but with appliance 200 positioned within the mouth 302 of the patient 300 and applied or placed on the maxillary teeth 326 and mandibular teeth 330. In this example, further the appliance 200 includes a tongue support 164, 184. The appliance 200 includes the positioning of the mouth 302 in an open position formed in place showing the opening of the mouth at the angle beta β to form airway cavity 208. Further, the appliance 200 include the appliance offset σ that was determined by the health care provider that in this embodiment having the lower jaw 328 and mandibular teeth 330 moved forward relative to the maxillary jaw 324 and maxillary teeth 326 by the predetermined amount of the appliance offset σ. In this manner, the forward positioning of the lower jaw 328 opens the pharynx 320 during appliance 200 use. Further, in this exemplary embodiment, the optional tongue support 164, 184 is included and configured to hold the tongue 310 in a forward position, thereby further opening the airway 312 of the patient as compared to that of FIG. 10. As noted, the tongue support 164, 184 is optional and may not be required for all patients 300 or their sleep apnea treatment.

Figure 12:
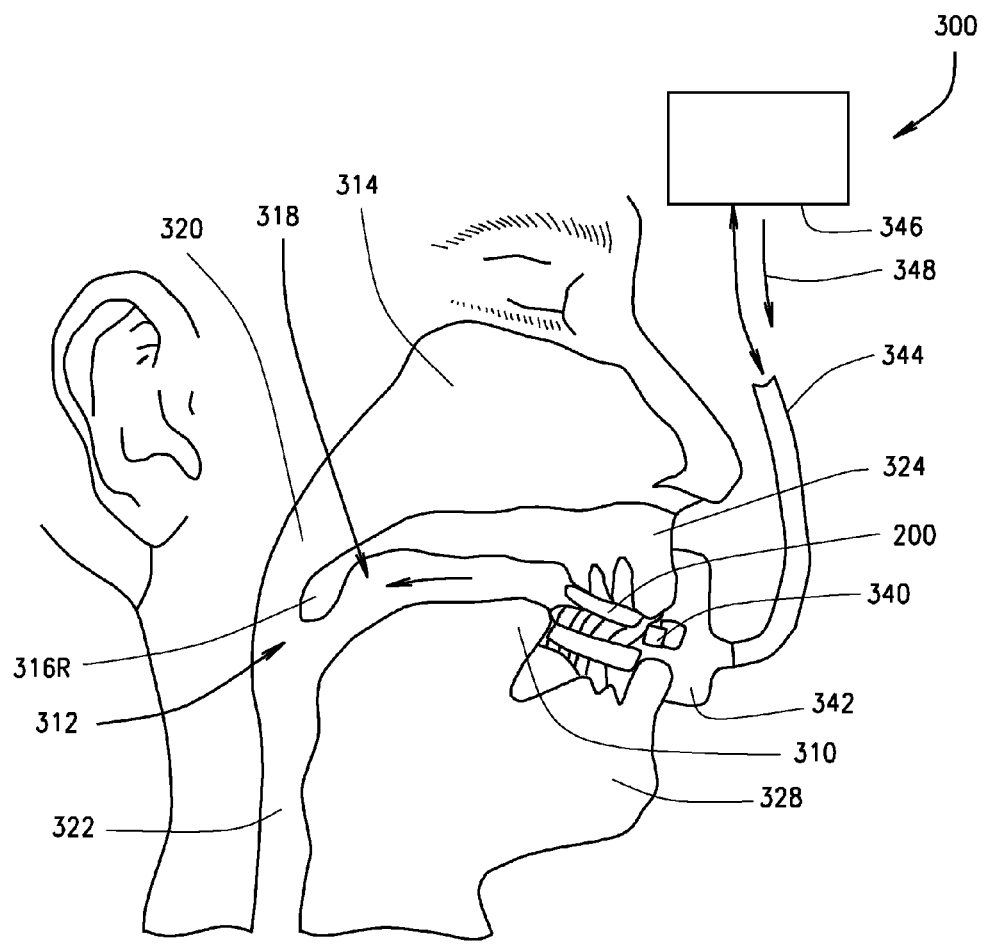
FIG. 12 is a side diagram of a patient with an appliance having a connector or adaptor for coupling to a positive airway pressure machine for receiving positive pressure through the orifice of the appliance during use by the patient.

In some cases, the patient may have also been prescribed a continuous positive airway pressure (CPAP) treatment wherein a CPAP machine provides air pressure to the airways during sleep. In such cases, the appliance 200 can include a connector or adaptor 340 which is coupled to or attachable to the appliance 200 or for attaching a CPAP coupler 342 for a mask or a tube 344 each of which are connected to a CPAP machine 346. This is shown in FIG. 12 where the CPAP machine 324 provides positive pressure airflow 348 to an air tube 344 that is connected to the mask connector 342 which is attached to the adaptor 340 of appliance 200. This results in the patient 300 receiving at least a portion of positive air pressure 350 within the airways during use of the appliance 200. The appliance 200 as addressed above benefits the use of the CPAP machine 346 by moving the lower jaw 328 forward of the upper jaw 324 to physically open the air passage 312 while the received positive air pressure 350 further opens air passage 312 as well as other airways during sleep. The appliance 200 can be adapted to include an adaptor 340 that directly attaches to the CPAP machine 346 rather than requiring the patient 300 to have a nasal mask over the nose.

In other embodiments, a method of treating sleep apnea using the above described oral appliances. The patient is analyzed to determine the best fit as described herein, the appliance is manufactured as described herein and the patient places the prepared appliance is his mouth during sleep as described herein for the treatment of sleep apnea. As noted above, the above various appliances can be used to treat gum/periodontal disease simultaneously while treating sleep apnea or for application of a tooth whitening solution or compound.

Another embodiment includes a method of manufacturing an oral appliance for treating sleep apnea of a patient, the patient having maxillary teeth located on an upper jaw, mandibular teeth on a lower jaw, a mouth cavity formed by the upper jaw and the lower jaw containing the maxillary teeth, the mandibular teeth, a tongue and an airway defined by the throat passage. The method includes taking an upper impression of the maxillary teeth and a soft gum tissue proximate to and surrounding the maxillary teeth of the patient, and preparing a maxillary cast from the upper impression. The method also includes taking a lower impression of the mandibular teeth and a soft gum tissue proximate to and surrounding the mandibular teeth of the patient and preparing a mandibular cast from the lower impression.

The process of preparing the upper and lower trays can include molding a resilient elastomeric material to the maxillary cast and molding a resilient elastomeric material to the mandibular cast. While this process can include any suitable material, a moldable resilient soft plastic elastomeric material or similar soft material is often preferred.

The method further includes determining a functional position of the lower jaw relative to the upper jaw of the patient to open the airway defined by the throat passage. Next the upper tray from the maxillary cast is prepared and the method includes preparing a lower tray from the mandibular cast. The method includes embedding the upper tray in stone forming an upper tray stone cast leaving only a portion of the upper tray exposed, embedding the lower tray in stone forming a lower tray stone cast and leaving only a portion of the lower tray exposed. The method further includes placing the embedded upper tray and the embedded lower tray in an articulator, positioning the embedded upper tray and the embedded lower tray in the articulator for alignment in the determined functional position and coupling the exposed portion of the upper tray to the exposed portion of the lower tray forming an oral appliance having a unified body. The method then includes removing the stone in which oral appliance is embedded.

The method of manufacture of the appliance can also include positioning the embedded upper tray and the embedded lower tray in the articulator with alignment of the tongue support for positioning the tongue to prevent the tongue from obstructing the open airway resulting from the determining of the functional position.

This process can include positioning the embedded upper tray and the embedded lower tray and coupling the exposed portion of the upper tray to the exposed portion of the lower tray each includes forming a orifice between a front of the upper tray and a front of the lower tray. As addressed above, this can include forming an adaptive interface to the orifice for selectively coupling to an oral device associated with a sleep apnea positive pressure machine.

The method of manufacturing can include coupling the exposed portion of the upper tray to the exposed portion of the lower tray by heating of each with a torch or other suitable heating source, or through use of an adhesive or similar attachment mechanism. Where heat is applied, the method of coupling can include adding an amount of a suitable bonding agent, such as ethylene vinyl acetate (EVA) material, into a space between the exposed portion of the upper tray and the exposed portion of the lower tray when they are heated, and such that once they are cooled, the bonding agent fixedly couples the upper tray to the lower tray to form the monolithic or unibody of the appliance.

The method of manufacturing can also include taking an impression of the tongue of the patient and preparing one or more tongue support fixtures from the tongue impression. This can be by any suitable method and can include, but is not limited to a wax impression. This can also include taking the impression of a back edge of the tongue and preparing the tongue support fixture includes preparing a fixture for resting behind the back edge of the tongue for holding the tongue in a forward position and inhibiting the backward movement of the tongue when the oral appliance is placed in the patient's mouth.

The tongue support fixture or fixtures can be coupled to at least one of the exposed portion of the upper tray or between and the exposed portion of the lower tray to form a unibody oral appliance with integrated tongue support. As such this step of attachment and formation of the tongue support into the monolithic or unibody oral appliance can take place after the embedded upper tray and the embedded lower tray is placed in the articulator.

A noted, there can be a single tongue support in which case the tongue support could expand or extend across the interior of the mouth between two opposing sides of the appliance. In other embodiments, the tongue support fixture includes a right fixture portion and a left fixture portion with the right fixture portion extending towards the tongue from a right inner side of the appliance to which it is coupled and a left fixture portion would extend towards the tongue from a left inner side of the appliance to which it is coupled.

The method of manufacture of the appliance can include coupling the tongue support to the other portions of the appliance either before or after coupling of the upper tray to the lower tray by any suitable means. In one exemplary embodiment, the method includes heating at least a portion of the exposed portion of the upper tray or the lower tray with a torch and adding an amount suitable material such as ethylene vinyl acetate (EVA) material, by way of example, between the at least one of the exposed portion of the upper tray and the exposed portion of the lower tray and the tongue support.

In some embodiments of the method of manufacture, when taking the upper impression of the maxillary teeth, this step can include taking an impression of a soft gum tissue proximate to and surrounding the maxillary teeth of the patient and the mandibular teeth of the patient in forming the upper and lower trays. In this manner the upper and lower trays can be formed to not only cover the crowns of the teeth but also a portion of the soft gum tissue proximate to each tooth. As such, in this method the process of preparing a maxillary stone cast from the upper impression would include the soft gum tissue proximate the maxillary teeth and the process of preparing the mandibular stone case from the lower impression includes soft gum tissue proximate the mandibular teeth. In these embodiments, the process of preparing the upper tray would include forming the upper tray to include a portion covering the soft gum tissue proximate to and surrounding the maxillary teeth and would include preparing the lower tray to include a portion covering the soft gum tissue proximate to and surrounding the mandibular teeth. In such embodiments, as the trays include a portion of the soft gum tissue proximate the teeth, the process can also include preparing the upper tray to forming a seal a portion covering the soft gum tissue proximate to and surrounding the maxillary teeth. Similarly, the process of preparing the lower tray can include forming a portion of the lower tray to cover the soft gum tissue proximate to and surrounding the mandibular teeth.

The method in this regard can include defining an upper elongated seal groove along an upper gum line and defining a lower elongated seal groove along a lower gum line. The processes of preparing the upper tray and lower tray include forming a raised seal on the along the gum lines as defined by the elongated seal grooves in the maxillary cast and the mandibular cast.

The process includes determining a functional position of the lower jaw relative to the upper jaw of the patient to open the airway defined by the throat passage including positioning the lower jaw forward and the downward to open the mouth from a closed mouth position to produce a forward protrusion of the mandible relative to the maxilla and an space between a portion of the front maxillary teeth and the front mandibular teeth forming a orifice. This can include determining the functional position includes determining a best functional relationship of the lower jaw relative to the upper jaw and a maxilla and a head of the patient relative to the spine of the patient. This can include, but is not limited to taking a bite registration at the time of taking the upper impression and the lower impression and determining the functional position is a function of the occlusion identified by the bite registration balanced with a determination of muscles of mastification and jaw joint relationship.

As disclosed herein, the present oral tray and method of manufacture and use is for treating sleep disorders and sleep apnea/hypopnea through the use of custom formed dental trays affixed at the patient best functional mandibular/maxillary relationship. Joint problems are first addressed to allow a patient with TMJ dysfunction to correct the compromises in the function of the mandibular/maxillary relationship so they are able to function and have a better functional association. These problems include internal and external joint compromises resulting in being unable to open fully, and a mandibular position that is compromised and unable to functional adequately or normally. These compromises make it impossible for the structures to functional adequately and can cause limitations in structural and functional dimensions, including airway dimensions. It is possible to reestablish the functional relationships with a combination of physical medicine modalities, orthotics and patient cooperation to acquire a best functional position. In some instances surgery, such as disc repositioning or maxillary and mandibular surgery or tonsil, adenoid removal may be required. The patient's best functional mandibular/maxillary relationship is established with a combination of intraoral orthotics, physical medicine or other means. This relationship is evaluated to ascertain the structural and functional interactions to be as ideal as possible. Patient's casts, models, molds or other representations of the teeth are related to one another at this functional posture. Custom formed trays, such as a PerioTray™, are fabricated on the models, casts or representations of the teeth at this relationship and are combined into one appliance to maintain this association when placed over the patient's teeth in the mouth.

The trays are fabricated for the upper and lower teeth. These are made at the patient's best functional relationship (joint, muscle, and upper quadrant function) and are made as one appliance, instead of two. The tongue shows the airway in the front region. Once the upper and lower trays are initially made, they are coupled together as one appliance so that the patient's mandibular/maxillary relationship is established at the best joint, muscle and functional position. Then when the patient sleep with the appliance in place these best functional associations are maintained and our research is showing a decrease or elimination of sleep apnea events, better oxygen blood levels, less muscle hyperactivity, no grinding and the heart rates have fluctuated much less.

A normal bite registration is a substance (in this case a special bite registration wax) that fits between the teeth. That does not allow us to observe where the tongue sits when the patient is awake. This initial bite registration is different in we mold the wax across the patient's palate so it is in one piece and will serve as an impression tray for taking an impression of the tongue. We added a second impression material (after the functional bite was established) that gives us an impression of the dorsal side of the tongue and we go as far back as the patient's gag reflex will allow. (We can apply a 6% lidocaine gel to the tongue and override some of the gag reflex). This gives us an impression of the tongue and we are in particular looking for the most posterior and lateral border. We make an EVA flange that will go around the lateral border of the tongue much the same as your fingers may go around a cantaloupe when you are picking it up with both hands. This flange is positioned around the stone impression of the dorsal surface of the tongue that we pour up and position with the teeth models so the processed flanges serves to help hold the tongue in position when the patient sleeps. All of the surfaces we do not want to distort are imbedded in stone and the EVA material is then affixed to the upper and lower trays with a heat process.

When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

Those skilled in the art will recognize that various changes can be made to the exemplary embodiments and implementations described above without departing from the scope of the disclosure. Accordingly, all matter contained in the above description or shown in the accompanying drawings should be interpreted as illustrative and not in a limiting sense.

It is further to be understood that the processes or steps described herein are not to be construed as necessarily requiring their performance in the particular order discussed or illustrated. It is also to be understood that additional or alternative processes or steps may be employed.

What is claimed is:

1. A method of manufacturing an oral appliance for treating sleep apnea of a patient, the patient having maxillary teeth located on an upper jaw, mandibular teeth on a lower jaw, a mouth cavity formed by the upper jaw and the lower jaw containing the maxillary teeth, the mandibular teeth, a tongue and an airway defined by the throat passage, the method comprising:
    preparing a tongue support fixture;
    taking an upper impression of the maxillary teeth and a soft gum tissue proximate to and surrounding the maxillary teeth of the patient;
    preparing a maxillary cast from the upper impression;
    taking a lower impression of the mandibular teeth and a soft gum tissue proximate to and surrounding the mandibular teeth of the patient;
    preparing a mandibular cast from the lower impression;
    determining a functional position of the lower jaw relative to the upper jaw of the patient to open the airway defined by the throat passage;
    preparing an upper tray from the maxillary cast;
    preparing a lower tray from the mandibular cast;
    coupling the tongue support to at least one of the upper tray and the lower tray;
    embedding the upper tray in stone forming an upper tray stone cast, said embedding the upper tray leaving only a portion of the upper tray exposed;
    embedding the lower tray in stone forming a lower tray stone cast, said embedding the lower tray leaving only a portion of the lower tray exposed;
    placing the embedded upper tray and the embedded lower tray in an articulator;
    positioning the embedded upper tray and the embedded lower tray in the articulator for alignment in the determined functional position;
    coupling the exposed portion of the upper tray to the exposed portion of the lower tray forming the oral appliance having a unified body; and
    removing the stone in which oral appliance is embedded.

2. The method of claim 1, further comprising:
    taking an impression of the tongue of the patient, wherein the preparing of the tongue support fixture utilizes the taken impression of the tongue;
    wherein the coupling the tongue support includes coupling the tongue support to at least one of the exposed portion of the upper tray and the exposed portion of the lower tray to form a unibody oral appliance with the integrated tongue support and wherein this step is after placing the embedded upper tray and the embedded lower tray in the articulator.

3. The method of claim 2 wherein taking the impression of the tongue includes taking a wax impression.

4. The method of claim 2 wherein taking the impression of the tongue includes taking an impression of a back edge of the tongue and preparing the tongue support fixture includes preparing a fixture for resting behind the back edge of the tongue for holding the tongue in a forward position and inhibiting the backward movement of the tongue when the oral appliance is placed in the patient's mouth.

5. The method of claim 1 wherein the tongue support fixture includes a right fixture portion and a left fixture portion, wherein the right fixture portion is coupled to a right side of at least one of the lower tray and the upper tray and the left fixture portion is coupled to a left side of at least one of the lower tray and the upper tray.

6. The method of claim 1 wherein coupling the tongue support includes heating at least a portion of the exposed portion of the upper tray or the lower tray with a torch and adding an amount of ethylene vinyl acetate (EVA) material between the at least one of the exposed portion of the upper tray and the exposed portion of the lower tray and the tongue support.

7. The method of claim 1 wherein positioning the embedded upper tray and the embedded lower tray in the articulator including alignment of the tongue support for positioning the tongue to prevent the tongue from obstructing the open airway resulting from the determining of the functional position.

8. The method of claim 1 wherein taking the upper impression of the maxillary teeth includes taking an impression of a soft gum tissue proximate to and surrounding the maxillary teeth of the patient and taking the lower impression of the mandibular teeth includes taking an impression of a soft gum tissue proximate to and surrounding the mandibular teeth of the patient;
    wherein preparing a maxillary stone cast from the upper impression includes the soft gum tissue proximate the maxillary teeth and preparing the mandibular stone cast from the lower impression includes soft gum tissue proximate the mandibular teeth; and
    wherein preparing the upper tray includes a portion covering the soft gum tissue proximate to and surrounding the maxillary teeth and preparing the lower tray includes a portion covering the soft gum tissue proximate to and surrounding the mandibular teeth.

9. The method of claim 1 wherein preparing the upper tray includes forming a portion covering the soft gum tissue proximate to and surrounding the maxillary teeth providing a seal thereto and preparing the lower tray includes a portion covering the soft gum tissue proximate to and surrounding the mandibular teeth providing a seal thereto.

10. The method of claim 1, wherein positioning the embedded upper tray and the embedded lower tray and coupling the exposed portion of the upper tray to the exposed portion of the lower tray each includes forming a orifice between a front of the upper tray and a front of the lower tray.

11. The method of claim 10, further comprising forming an adaptive interface to the orifice for selectively coupling to an oral device associated with a sleep apnea positive pressure machine.

12. The method of claim 1 wherein coupling the exposed portion of the upper tray to the exposed portion of the lower tray includes heating of each with a torch.

13. The method of claim 12 wherein coupling using heating with a torch includes adding an amount of ethylene vinyl acetate (EVA) material into a space between the exposed portion of the upper tray and the exposed portion of the lower tray.

14. The method of claim 1 wherein preparing the upper tray includes molding a resilient elastomeric material to the maxillary cast and preparing the lower tray includes molding a resilient elastomeric material to the mandibular cast.

15. The method of claim 1, further comprising:
defining an upper elongated seal groove along an upper gum line by removing an amount of the maxillary cast; and
defining a lower elongated seal groove along a lower gum line by removing an amount of the mandibular cast,
wherein preparing the upper tray includes forming a raised seal on the upper tray along the gum line as defined by the upper elongated seal groove of the maxillary cast and preparing the lower tray includes forming a raised seal on the lower tray along the gum line as defined by the lower elongated seal groove of the mandibular cast.

16. The method of claim 1 wherein determining a functional position of the lower jaw relative to the upper jaw of the patient to open the airway defined by the throat passage including positioning the lower jaw forward and the downward to open the mouth from a closed mouth position to produce a forward protrusion of the mandible relative to the maxilla and a space between a portion of the front maxillary teeth and the front mandibular teeth forming a orifice.

17. The method of claim 1 wherein determining the functional position includes determining a best functional relationship of the lower jaw relative to the upper jaw and a maxilla and a head of the patient relative to the spine of the patient.

18. The method of claim 1, further comprising
taking a bite registration at the time of taking the upper impression and the lower impression,
wherein determining the functional position is a function of the occlusion identified by the bite registration balanced with a determination of muscles of mastification and jaw joint relationship.

19. A method of manufacturing an oral appliance for treating sleep apnea of a patient, the patient having maxillary teeth located on an upper jaw, mandibular teeth on a lower jaw, a mouth cavity formed by the upper jaw and the lower jaw containing the maxillary teeth, the mandibular teeth, a tongue and an airway defined by the throat passage, the method comprising:
taking an upper impression of the maxillary teeth and a soft gum tissue proximate to and surrounding the maxillary teeth of the patient;
taking an impression of the tongue of the patient;
preparing a maxillary cast from the upper impression;
taking a lower impression of the mandibular teeth and a soft gum tissue proximate to and surrounding the mandibular teeth of the patient;
preparing a mandibular cast from the lower impression;
determining a functional position of the lower jaw relative to the upper jaw of the patient to open the airway defined by the throat passage;
preparing an upper tray from the maxillary cast;
preparing a lower tray from the mandibular cast;
preparing a tongue support fixture from the tongue impression;
embedding the upper tray in stone forming an upper tray stone cast, said embedding the upper tray leaving only a portion of the upper tray exposed;
embedding the lower tray in stone forming a lower tray stone cast, said embedding the lower tray leaving only a portion of the lower tray exposed;
placing the embedded upper tray and the embedded lower tray in an articulator;
positioning the embedded upper tray and the embedded lower tray in the articulator for alignment in the determined functional position;
coupling the exposed portion of the upper tray to the exposed portion of the lower tray forming an oral appliance having a unified body;
coupling the tongue support to at least one of the exposed portion of the upper tray and the exposed portion of the lower tray to form the oral appliance with integrated tongue support and having a unified body; and
removing the stone in which oral appliance is embedded.

20. The method of claim 19 wherein taking the upper impression of the maxillary teeth includes taking an impression of a soft gum tissue proximate to and surrounding the maxillary teeth of the patient and taking the lower impression of the mandibular teeth includes taking an impression of a soft gum tissue proximate to and surrounding the mandibular teeth of the patient;
wherein preparing a maxillary stone cast from the upper impression includes the soft gum tissue proximate the maxillary teeth and preparing the mandibular stone case from the lower impression includes soft gum tissue proximate the mandibular teeth; and
wherein preparing the upper tray includes a portion defining a seal covering the soft gum tissue proximate to and surrounding the maxillary teeth and preparing the lower tray includes a portion covering the soft gum tissue proximate to and surrounding the mandibular teeth.

21. A method of manufacturing an oral appliance for treating sleep apnea of a patient, the patient having maxillary teeth located on an upper jaw, mandibular teeth on a lower jaw, a mouth cavity formed by the upper jaw and the lower jaw containing the maxillary teeth, the mandibular teeth, a tongue and an airway defined by the throat passage, the method comprising:
taking an impression of the tongue of the patient;
taking an upper impression of the maxillary teeth and a soft gum tissue proximate to and surrounding the maxillary teeth of the patient and includes taking an impression of a soft gum tissue proximate to and surrounding the maxillary teeth of the patient;

preparing a maxillary cast from the upper impression including the soft gum tissue proximate the maxillary teeth;

taking a lower impression of the mandibular teeth and a soft gum tissue proximate to and surrounding the mandibular teeth of the patient and includes taking an impression of a soft gum tissue proximate to and surrounding the mandibular teeth of the patient;

preparing a mandibular cast from the lower impression including the soft gum tissue proximate the mandibular teeth;

determining a functional position of the lower jaw relative to the upper jaw of the patient to open the airway defined by the throat passage;

preparing an upper tray from the maxillary cast including a portion covering the soft gum tissue proximate to and surrounding the maxillary teeth;

preparing a lower tray from the mandibular cast including a portion covering the soft gum tissue proximate to and surrounding the mandibular teeth, wherein preparing at least one of the upper tray and the lower tray includes forming a seal a portion covering the soft gum tissue proximate to and surrounding the maxillary teeth or mandibular teeth respectively;

preparing a tongue support fixture from the tongue impression;

embedding the upper tray in stone forming an upper tray stone cast, said embedding the upper tray leaving only a portion of the upper tray exposed;

embedding the lower tray in stone forming a lower tray stone cast, said embedding the lower tray leaving only a portion of the lower tray exposed;

placing the embedded upper tray and the embedded lower tray in an articulator;

positioning the embedded upper tray and the embedded lower tray in the articulator for alignment in the determined functional position;

coupling the tongue support to at least one of the upper tray and the lower tray;

coupling the exposed portion of the upper tray to the exposed portion of the lower tray, the coupling including applying heat to the exposed portion of the upper tray to the exposed portion of the lower tray and forming the oral appliance having a unified body; and removing the stone in which oral appliance is embedded.

22. The method of claim 21 wherein taking the impression of the tongue includes taking a wax impression.

23. The method of claim 21 wherein taking the impression of the tongue includes taking an impression of a back edge of the tongue and preparing the tongue support fixture includes preparing a fixture for resting behind the back edge of the tongue for holding the tongue in a forward position and inhibiting the backward movement of the tongue when the oral appliance is placed in the patient's mouth.

24. The method of claim 21 wherein the tongue support fixture includes a right fixture portion and a left fixture portion, wherein the right fixture portion is coupled to a right side of at least one of the lower tray and the upper tray and the left fixture portion is coupled to a left side of at least one of the lower tray and the upper tray.

25. The method of claim 21 wherein coupling the tongue support includes heating at least a portion of the exposed portion of the upper tray or the lower tray with a torch and adding an amount of ethylene vinyl acetate (EVA) material between the at least one of the exposed portion of the upper tray and the exposed portion of the lower tray and the tongue support.

26. The method of claim 19 wherein taking the impression of the tongue includes taking a wax impression.

27. The method of claim 19 wherein taking the impression of the tongue includes taking an impression of a back edge of the tongue and preparing the tongue support fixture includes preparing a fixture for resting behind the back edge of the tongue for holding the tongue in a forward position and inhibiting the backward movement of the tongue when the oral appliance is placed in the patient's mouth.

28. The method of claim 19 wherein the tongue support fixture includes a right fixture portion and a left fixture portion, wherein the right fixture portion is coupled to a right side of at least one of the lower tray and the upper tray and the left fixture portion is coupled to a left side of at least one of the lower tray and the upper tray.

29. The method of claim 19 wherein coupling the tongue support includes heating at least a portion of the exposed portion of the upper tray or the lower tray with a torch and adding an amount of ethylene vinyl acetate (EVA) material between the at least one of the exposed portion of the upper tray and the exposed portion of the lower tray and the tongue support.

30. A method of manufacturing an oral appliance for treating sleep apnea of a patient, the patient having maxillary teeth located on an upper jaw, mandibular teeth on a lower jaw, a mouth cavity formed by the upper jaw and the lower jaw containing the maxillary teeth, the mandibular teeth, a tongue and an airway defined by the throat passage, the method comprising:

taking an upper impression of the maxillary teeth and a soft gum tissue proximate to and surrounding the maxillary teeth of the patient;

preparing a maxillary cast from the upper impression;

taking a lower impression of the mandibular teeth and a soft gum tissue proximate to and surrounding the mandibular teeth of the patient;

preparing a mandibular cast from the lower impression;

determining a functional position of the lower jaw relative to the upper jaw of the patient to open the airway defined by the throat passage;

preparing an upper tray from the maxillary cast;

preparing a lower tray from the mandibular cast;

embedding the upper tray in stone forming an upper tray stone cast, said embedding the upper tray leaving only a portion of the upper tray exposed;

embedding the lower tray in stone forming a lower tray stone cast, said embedding the lower tray leaving only a portion of the lower tray exposed;

placing the embedded upper tray and the embedded lower tray in an articulator;

positioning the embedded upper tray and the embedded lower tray in the articulator for alignment in the determined functional position;

coupling the exposed portion of the upper tray and the exposed portion of the lower tray by heating the exposed portion of the upper tray and the exposed portion of the lower tray and forming the oral appliance having a unified body; and removing the stone in which oral appliance is embedded.

31. The method of claim 30 wherein coupling by heating includes applying a torch as the heating to the exposed portion of the upper tray and the exposed portion of the lower tray.

32. The method of claim 30 wherein coupling by heating includes adding an amount of a suitable heat induced bonding agent into a space between the exposed portion of the upper tray and the exposed portion of the lower tray during the process of heating, and after a cooling of the suitable heat induced bonding agent and the exposed portion of the upper tray and the exposed portion of the lower tray, the cooled bonding agent fixedly couples the upper tray to the lower tray to form the unified body.

33. The method of claim 32 wherein the method of adding the amount of suitable head induced bonding agent includes adding an amount of ethylene vinyl acetate (EVA) material.

* * * * *